United States Patent [19]

Melin et al.

[11] Patent Number: 4,504,469

[45] Date of Patent: Mar. 12, 1985

[54] VASOTOCIN DERIVATIVES

[75] Inventors: Per O. R. Melin, Malmö; Jerzy A. Trojnar, Vintrie, both of Sweden

[73] Assignee: Ferring AB, Malmö, Sweden

[21] Appl. No.: 561,920

[22] Filed: Dec. 15, 1983

[30] Foreign Application Priority Data

Dec. 21, 1982 [SE] Sweden .............................. 8207277
May 3, 1983 [SE] Sweden .............................. 8302505

[51] Int. Cl.³ ..................... A61K 37/00; C07C 103/52
[52] U.S. Cl. ................................. 514/11; 260/112.5 R
[58] Field of Search ................... 260/112.5 R; 424/177

[56] References Cited

U.S. PATENT DOCUMENTS

| 4,081,533 | 3/1978 | Cheesman | 424/177 |
| 4,163,011 | 7/1979 | Orts | 260/112.5 R |
| 4,367,225 | 1/1983 | Manning et al. | 260/112.5 R |
| 4,402,942 | 9/1983 | Melin | 260/112.5 R |

OTHER PUBLICATIONS

Schröder, et al., The Peptides II, 1966, 320 & 321.
Horiki et al.: "Synthesis of the Merrifield Resin . . . ", Chemistry Letters, 1978, pp. 165–168.
Larsson et al.: "Synthesis of O-Alkylated Lysin-vasopressins . . . ", J. of Medicinal Chem., 1978, vol. 21, No. 4, pp. 352–366.
Kaiser et al.: "Color Test for Detection of Free . . . ", Short Communications, Anal. Briochem. 34 (1970), pp. 595–598.
Koenig et al.: Chem. Ber. 103, 788–798 (1970) "Eine neue Methode zur Synthese von Peptiden: Aktivierung der Carboxylgruppe . . . ".
Merrifield: "Solid–Phase Peptide Synthesis. III. An Improved . . . " Biochemistry 3 (Sep. 1964), pp. 1385–1390.
Merrifield: "Solid–Phase Peptide Synthesis. I. The Synthesis . . . " J. Am. Chem. Soc. 85 (Jul. 1963), pp. 2149–2154.
Law et al.: "Synthesis of 2-p-Methoxyphenylalanine Oxytocin . . . " J. Am. Chem. Soc. 82 (Sep. 1960), pp. 4579–4581.
Sawyer et al.: Review, "Neurohypophysial Peptides—Design of Tissue . . . " Molecular and Cellular Endocrinology, 22 (1981) 117–134.

Primary Examiner—Delbert R. Phillips
Attorney, Agent, or Firm—Cushman, Darby & Cushman

[57] ABSTRACT

Novel vasotocin derivatives having an inhibitory effect on uterine contractions, pharmaceutical compositions containing these derivatives, and the use thereof in the therapeutical treatment of excessive muscle contractions in the uterus and described. The derivatives differ from vasotocin in that the structure of the original hormone has been modified at positions 1, 2 and, optionally, 4 and/or 8. The vasotocin derivatives thus have the formula

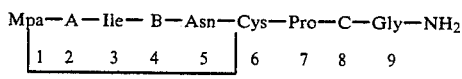

wherein
Mpa is a 3-mercaptopropionoyl residue (—S—CH$_2$—CH$_2$—CO—);
A is the peptide residue of L- or D-tyrosine-O-ethyl ether (in other words, 4-ethoxy-L or D-phenyl alanine, i.e. L- or D-Tyr(Et)), or of a hydrophobic D-amino acid, such as D-tyrosine(D-Tyr) or D-tryptophane(D-Trp);
Ile is the peptide residue of isoleucine;
B is the peptide residue of glutamine (Gln), treonine (Thr) or valine (Val);
Asn is the peptide residue of asparagin;
Cys is the peptide residue of cysteine;
Pro is the peptide residue of proline;
C is the peptide residue of L- or D-arginine (Arg), ornithine (Orn) or citrullin (Cit); and
Gly—NH$_2$ is the peptide residue of glycine amide.

9 Claims, No Drawings

VASOTOCIN DERIVATIVES

The present invention relates to novel vasotocin derivatives, i.e. such vasotocin derivatives as differ from the natural hormone in that the vasotocin structure has been modified at positions 1, 2 and, optionally, 4 and/or 8. The novel derivatives are competitive inhibitors blocking the receptors of the body, thereby making it difficult for the endogeneous hormones of the body to exert an agonistic effect. More particularly, these novel derivatives have an inhibitory effect on uterine contractions, and their inhibitory effect on vasopressin and on oxytocin induced uterus contractions has been tested on rats.

Another important aspect is that the derivatives according to the invention also inhibit the spontaneous contraction pattern of the uterus.

The vasotocin derivatives according to the invention are comprised by the following formula

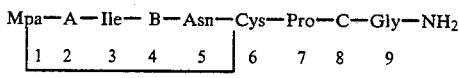

wherein
- Mpa is a 3-mercaptopropionoyl residue (—S—CH$_2$—CH$_2$—CO—);
- A is the peptide residue of L- or D-tyrosine-O-ethyl ether (in other words, 4-ethoxy-L or D-phenyl alanine, i.e. L- or D-Tyr(Et)), or of a hydrophobic D-amino acid, such as D-tyrosine (D-Tyr) or D-tryptophane (D-Trp);
- Ile is the peptide residue of isoleucine;
- B is the peptide residue of glutamine (Gln), treonine (Thr) or valine (Val);
- Asn is the peptide residue of asparagin;
- Cys is the peptide residue of cysteine;
- Pro is the peptide residue of proline;
- C is the peptide residue of L- or D-arginine (Arg), ornithine (Orn) or citrullin (Cit); and
- Gly—NH$_2$ is the peptide residue of glycine amide.

Like the natural hormone, the vasotocin derivatives according to the invention may have L-arginine at position 8, but may also have D-arginine, L-ornithine or L-citrullin. Like the natural vasotocin, the compounds according to the invention may have the peptide residue of glutamine or the peptide residue of threonin or valine at position 4. Deaminated cysteine at position 1 in vasotocin has been indicated as a 3-mercaptopropionyl residue (or dNH$_2$) in the compounds of this invention.

The property of a non-transducing agonist is believed to lie in the modification of the amino acid of the natural hormone at position 2 which, like other neurohypophysis hormones, are believed to be of great importance to the biological activity. If, at this position, the side chain of the normal amino acid is modified, the receptor does not accept the molecule as an agonist. In view hereof, the tyrosine which is present in natural vasotocin, has either been 0-alkylated, or the D-configuration thereof has been introduced (or both variants have been used). It appears from the above explanation that other hydrophobic D-amino acids may also be introduced at the said postion 2. As an example of these other hydrophobic amino acids, tryptophane has been used in the experimental section of the present specification.

The vasotocin hormone differs from the oxytocin hormone merely in respect of the amino acid at position 8. Oxytocin has leucine at position 8, and vasotocin has arginine at position 8. Among several other known oxytocin derivatives having an antagonistic effect on oxytocin induced uterus contractions, 1-desamino-(2-0-ethyl tyrosine)-oxytocin (called Antocin in the following) according to our U.S. Pat. No. 4,402,942 may be mentioned as the compound which comes closest to the novel vasotocin derivatives of the present invention.

Known pharmaceuticals capable of counteracting excessive muscle contractions in the uterus are β-receptor-agonists, prostaglandin synthesis inhibitors, calcium antagonists, and ethanol. All of these agents have non-specific effects and thus produce secondary effects.

The vasotocin derivatives of the present invention are of considerable clinical interest in cases of premature labour or excessive spasms in the uterus in connection with delivery and menstruation (partus praematurus, dysmenorrhea). Also Antocin has been said to have these characteristics, but in relation to Antocin the present group of vasotocin derivatives have the advantage that they are between 2 to about 18 times more potent than Antocin (in tests carried out on rat uterus in vivo). Hence, as compared to Antocin, only ½ to about 1/18 of the present vasotocin derivatives are required in order to obtain the same effect, and this makes the vasotocin derivatives of the present invention potentially extremely advantageous from the medical and also the economical point of view.

The characteristic features of the invention will appear from the appended claims.

The vasotocin derivatives according to the invention may be presented in the form of pharmaceutical preparations in which also pharmaceutically acceptable additives and/or diluents are included. Preferably, the vasotocin derivatives are administered dissolved in physiological saline solution by injection, infusion or by intranasal application.

The vasotocin derivatives according to the invention can be prepared in analogy with processes well known in the peptide field.

For example, the compounds according to the invention may be prepared in conventional manner by incremental coupling of amino acids to one another in the liquid phase, for instance in accordance with the technique reported by Law, H. B. & Du Vigneaud, V. in the Journal of the American Chemical Society 82, (1960) 4579–4581, Zhuze, A. L. Jošt, K., Kasafirek, E. & Rudinger, J. in the Collection of Czechoslovak Chemical Communications 29, (1963), 2648–2662, and modified by Larsson, L.-E., Lindeberg, G., Melin, P. & Pliška, V. in the Journal of Medicinal Chemistry 21, (1978), 352–356. Coupling of the amino acids to one another, whereby so-called peptide bonds are formed, may also be carried out by starting with a solid phase (usually a resin) to which the C-terminal of the first amino acid is coupled, whereupon the C-terminal of the next amino acid is coupled to the N-terminal of the first amino acid etc. Finally, the built-up peptide is released from the solid phase.

In the following Examples, use has been made of this so-called solid phase technique in accordance with what has been reported by Merrifield, R. B., J. Am. Chem. Soc. (1963) 85, 2149, Merrifield, R. B., Biochemistry (1964), 3, 1385 and Konig, W., Geiger, R., Chem. Ber. (1970) 103, 788.

Upon synthesis, 1% of cross-linked polystyrene resin (BioRad S-XI) having a 1.2 meq/g chloromethyl function loading has been used. This resin was subjected to a coupling reaction with BocGly in DMF (dimethyl formamide) with KF (potassium fluoride) as catalyst (Horiki, K. et al, Chemistry Letters, (1978), 165–168) to yield BocGly-O resin having a chloromethyl function loading of about 1 meq/g.

This product served as the starting material in all of the subsequent syntheses as described in the following Examples. All of the amino acids used were of L configuration, unless otherwise indicated.

EXAMPLE 1

1-β-mercaptopropionic acid-2-(4-ethoxy)-phenyl alanine-8-ornithine-vasotocin

[X=H, A=Tyr(Et); B=Gln; C=Orn]

BocGly resin (3.0 g, 3 meq) was placed in the reaction vessel of a Vega Model 50 semiautomatic peptide synthesizer. The peptide was built up by increments on the resin in accordance with Tables 1 and 2. Activation of the amino acid was carried out by dissolving 10 meq of a suitably protected amino acid, 15 meq of hydroxy benzotriazole and 10 meq of dicyclohexyl carbodiimide in DMF (70 ml), whereupon the mixture was left at room temperature for 1 h (asparagine and glutamine were activated at 0° C. for 15 min), whereupon the precipitate was filtered off, and the filtrate was treated as the activated amino acid in Table 1 (step 7). The completion of the coupling step was checked by the method of Kaiser (Anal. Biochem. 34, 595 (1970)) after the cycle had been completed (step 9). If the test was positive (coupling yield below 99%), the cycle was repeated, starting from step 7.

If the test was negative, the termination procedure was performed according to Table 2.

When the whole sequence had been coupled, the resin was placed on a filter and washed repeatedly with methanol. The dried product was placed in a glass vessel and cooled in an ethanol-dry ice bath and suspended in methanol (about 100 ml). The mixture was then saturated with sodium-dried ammonia to achieve approximately 50% concentration. Then the vessel was placed in a steel cylinder and left at room temperature for two days. After the pressure had been relieved, the product was filtered, and the residue was extracted with hot (about 100° C.) DMF (2×100 ml). The filtrate and the extract were combined and evaporated. The residue was dissolved in a small amount of hot DMF, and methanol was added to the coupling point. The precipitate was collected by filtration and washed on the filter with methanol. After drying in vacuum, the purity was checked by thin-layer chromatography.

Yield about 2.8 g.

100 mg of the above described protected peptide were placed in a 100 ml round-bottom flask, and dry nitrogen was flushed through for about 15 min. 50 ml of sodium-dried ammonia were distilled in, and the protective group was removed from the product by adding sodium until blue colour remained in the solution for 15 sec. The excess of sodium was destroyed by adding ammonium chloride. Ammonia was removed in a nitrogen stream, and the residue was dissolved in 1 liter of methanol. The pH of the solution was adjusted to about 4 with concentrated acetic acid, and the solution was then titrated with 0.1 mM of iodine in methanol to brownish colour. The mixture was stirred with 3 g of Dowex 50×2 ion exchanger in chloride form for 10 min at room temperature. The ion exchanger was removed by filtration, and the filtrate was evaporated to dryness. The residue was dissolved in 3 ml of 20% acetic acid and purified by chromatography on Sephadex G-25 with 20% acetic acid as eluent. The final purification was achieved by reverse phase HPLC.

The purity of the product was determined on a HPCL column μ-Bondapak C-18 in 45% ethanol and 55% 5 mM trifluoro acetic acid in water. The column was supplied by Water Associates, Inc., Millford, Mass., U.S.A. The purity of the product was also shown by amino acid analysis.

Amino acid analysis: Asp: 1.04, Glu: 1.04, Pro: 1.00, Gly: 1.01, Ile: 1.02, Tyr: 0.91, Orn: 0.98.

By employing procedures similar to those described in Example 1, the compounds indicated in the following Examples were synthesized.

EXAMPLE 2

1-β-mercaptopropionic acid-2-(4-ethoxy)-D-phenyl alanine-8-arginine vasotocin

[X=H, A=D-Tyr(Et); B=Gln; C=Arg]

Amino acid analysis: Asp: 1.00, Glu: 1.01, Pro: 0.98, Gly: 0.95, ½ Cys: 1.06, Ile: 1.02, Tyr: 1.00, Arg: 0.98

EXAMPLE 3

1-β-mercaptopropionic acid-2-(4-ethoxy)-phenyl alanine-8-citrullin vasotocin

[A=Tyr(Et); B=Gln; C=Cit];

Amino acid analysis: Asp: 1.0, Glu: 0.87, Pro: 0.9, Gly: 1.0, Ile: 0.83, Tyr: 0.52, Cit: 0.73, NH$_3$: 3.2

EXAMPLE 4

1-β-mercaptopropionic acid-2-(4-ethoxy)-phenyl alanine-4-valine-8-arginine vasotocin

[A=Tyr(Et); B=Val; C=Arg];

Amino Acid analysis: Asp: 0.94, Pro: 0.94, Gly: 1.0, Val: 1.10, Ile: 0.98, Tyr: 0.89, Arg: 1.01, NH$_3$: 2.1

EXAMPLE 5

1-β-mercaptopropionic acid-2-(4-ethoxy)-phenyl alanine-4-treonine-8-arginine vasotocin

[A=Tyr(Et); B=Thr; C=Arg];

Amino acid analysis: Asp: 0.99, Thr: 0.89, Pro: 1.10, Gly: 1.0, Ile: 0.95, Tyr: 0.90, Arg: 1.05, NH$_3$: 2.2

EXAMPLE 6

1-β-mercaptopropionic acid-2-(4-ethoxy)-phenyl alanine-4-valine-8-ornithine vasotocin

[A=Tyr(Et); B=Val; C=Orn];

Amino acid analysis: Asp: 1.07, Pro: 1.05, Gly: 1.11, Val: 0.87, Ile: 0.87, Tyr: 1.02, Orn: 1.02 (A peak between ½ Cys and Val interferes with Val)

EXAMPLE 7

1-β-mercaptopropionic acid-2-(4-ethoxy)-D-phenyl alanine-8-arginine vasotocin

[A=D—Tyr(Et); B=Gln; C=Arg];

Amino acid analysis: Asp: 1.00, Glu: 1.01, Pro: 0.98, Gly: 0.95, ½ Cys: 1.06, Ile: 1.02, Tyr: 1.00, Arg: 0.98

EXAMPLE 8

1-β-mercaptopropionic acid-2-D-tryptophane-4-valine-8-arginine vasotocin

[A=D—Trp; B=Val; C=Arg];

Amino acid analysis: Asp: 0.99, Val: 1.01, Pro: 0.94, Gly: 1.00, ½ Cys: 1.95, Ile: 0.80, Arg: 1.03

EXAMPLE 9

1-β-mercaptopropionic acid-2-(4-ethoxy)-D-phenyl alanine-4-valine-8-D-arginine vasotocin

[A=D—Tyr(Et); B=Val; C=D—Arg];

Amino acid analysis: Asp: 0.99, Pro: 0.90, Gly: 1.00, Val: 0.98, Ile: 0.81, Tyr: 0.84, Arg: 1.03

EXAMPLE 10

1-β-mercaptopropionic acid-2-(4-ethoxy)-D-phenyl alanine-4-valine-8-ornithine vasotocin

[A=D—Tyr(Et); B=Val; C=Orn];

Amino acid analysis: Asp: 0.99, Pro: 1.00, Gly: 1.00, ½ Cys: 1.00, Val: 0.98, Ile: 0.80, Tyr: 0.85, Orn: 0.94

EXAMPLE 11

1-β-mercaptopropionic acid-2-(4-ethoxy)-D-phenyl alanine-4-treonine-8-ornithine vasotocin

[A=D—Tyr(Et); B=Thr; C=Orn];

Amino acid analysis: Asp: 0.92, Thr: 0.93, Pro: 0.94 Gly: 1.00, ½ Cys: 0.92, Ile: 0.95, Tyr: 0.86, Orn: 1.01

EXAMPLE 12

1-β-mercaptopropionic acid-2-D-tryptophane-4-treonine-8-D-arginine vasotocin

[A=D—Trp; B=Thr; C=D—Arg];

Amino acid analysis: Asp: 0.98, Thr: 0.98, Pro: 0.99, Gly: 1.00, ½ Cys: 1.08, Ile: 0.95, Trp: 0.64, Arg: 0.99

EXAMPLE 13

1-β-mercaptopropionic acid-2-D-tyrosine-4-valine-8-ornithine vasotocin

[A=D—Tyr; B=Val; C=Orn];

Amino acid analysis: Asp: 0.99, Pro: 0.91, Gly: 1.00, ½ Cys: 1.00, Val: 0.97, Ile: 0.80, Tyr: 0.95, Orn: 0.98

The compounds according to Examples 14 and 15 as indicated below were also prepared in analogy with the process according to Example 1, but no amino acid analysis of the compounds was carried out.

EXAMPLE 14

1-β-mercaptopropionic acid-2-D-tryptophane-4-valine-8-ornithine vasotocin

[A=D—Trp; B=Val; C=Orn];

EXAMPLE 15

1-β-mercaptopropionic acid-2-D-tryptophane-4-treonine-8-ornithine vasotocin

[A=D—Trp; B=Thr; C=Orn];

TABLE 1

Solid phase synthesis

| Step | Solvent/Reagent | Vol. [ml] | Time [min] | Number of cycles |
|---|---|---|---|---|
| 1 | Dichloromethane | 70 | 3 | 2 |
| 2 | 50% trifluoro acetic acid/ dichloromethane | 70 | 15 | 2 |
| 3 | Isopropanol | 70 | 3 | 2 |
| 4 | Dichloromethane | 70 | 3 | 2 |
| 5 | 10% diisopropylethylamine in dichloromethane | 70 | 3 | 2 |
| 6 | Dichloromethane | 70 | 3 | 2 |
| 7 | Activated amino acid | 70 | 120* | 1 |
| 8 | Isopropanol | 70 | 3 | 2 |
| 9 | Dichloromethane | 70 | 3 | 2 |

*30 for BocAsn and BocGln

TABLE 2

Termination procedure

| Step | Solvent/Reagent | Vol. [ml] | Time [min] | Number of cycles |
|---|---|---|---|---|
| 1 | IM Imidazole: dichloromethane + acetic acid anhydride | 70 7 | 30 | 1 |
| 2 | Isopropanol | 70 | 3 | 2 |
| 3 | Dichloromethane | 70 | 3 | 4 |

The compounds prepared in accordance with the above Examples were kept in freeze-dried condition until they were utilized for the pharmacological tests accounted for in the following.

PHARMACOLOGICAL TESTS

The compounds according to the invention were investigated with regard to uterotonic potency on isolated rat uterus, using oxytocin as standard. The antagonistic properties of the compounds were also evaluated with the aid of this preparation. Also in vivo tests using oxytocin as the agonist were carried out, the results being compared with those obtained with Antocin.

IN VITRO TESTS ON RATS

Sprague Dawley rats (body weight approximately 250 g) in natural estrous were selected by vaginal smears. An approximately 20 mm long segment was cut from the middle of a uterine horn and mounted in an organ bath containing 10 ml of a modified Locke's solution of the following composition (mM:NaCl 153, KCl 5.63, $CaCl_2$ 0.541, $NaHCO_3$ 5.95 and glucose 2.78). The solution was gassed with 5% $CO_2$ in oxygen at 30° C. The uterine contractions were allowed to stabilize for 30 min. Contractions were recorded isometrically at a resting tension of 1.5 g using Grass force transducers (Ft. 03). The antagonistic potency of the analogs was were compared with the inhibition of the Antocin which was given the value 1.

TABLE 3

Vasotocin derivatives tested with regard to antagonistic activity on rat uterus in vitro and in vivo

| Example No. | Peptide | AD | Pressor | Uterus in vitro antagonist $pA_2$ | Uterus in vivo, compared with Antocin |
|---|---|---|---|---|---|
|  | $dNH_2$-2Tyr(Et)—OT (Antocin) | <0.2 | <0.1 | 7.2 |  |
| 5. | $dNH_2$-2Tyr(Et)—4-Thr 8-Arg—VT | 3.2 | 3.6 | 8.0 | 4 |
| 4. | $dNH_2$-2Tyr(Et)—4-Val- 8-Arg—VT | 7 | 0.5 | 8.5 | 5 |
| 3. | $dNH_2$-2Tyr(Et)—8- Cit—VT | 0.4 | <0.03 | 8.5 | 2 |
| 1. | $dNH_2$-2Tyr(Et)-8- Orn—VT | <1.3 | 1.4 | 8.4 | 5 |
| 7. | $dNH_2$-2Tyr(Et)—8- Arg—VT | 37.9 | 2.5 | 8.4 | 2 |
| 6. | $dNH_2$-2Tyr(Et—4- Val-8-Orn—VT | 0.4 | 0.9 | 7.6 | 1.0 |
| 2. | $dNH_2$-2-D-Tyr(Et)— 8-Arg—VT | 1.0 | 1.8 | 8.7 | 1.4 |
| 10. | $dNH_2$-2-D-Tyr(Et)— 4-Val—8-Orn—VT | 0.4 | 0.2 | 7.9 | 2.1 |
| 11. | $dNH_2$-2-D-Tyr(Et)— 4-Thr—8-Orn—VT | 2.5 | 2.4 | 8.3 | 4.0 |
| 9. | $dNH^2$-2-D-Tyr(Et)— 4-Val—8-D-Arg—VT | 0.5 | 0.3 | 8.6 | 5 |
| 8. | $dNH_2$-2-D-Trp-4-Val— 8-Arg—VT | 0.1 | 0.12 | 8.4 | 1 |
| 12. | $dNH_2$-2-D-Trp—4- Thr—8D-Arg—VT | 0.1 | 0.12 | 8.0 | 1.3 |
| 13. | $dNH_2$-2-D-Tyr—4- Val—8-Orn—VT | 1.2 | 1.6 | 8.2 | 4.4 |
| 14. | $dNH_2$-2-D-Trp—4- Val—8-Orn—VT | 0.03 | 0.03 | 7.9 | 7.9 |
| 15. | $dNH_2$-2-D-Trp—4- Thr—8-Orn—VT | 0.1 | 0.05 | 8.5 | 1.3 |

VT = vasotocin
OT = oxytocin calculated as $pA_2$ values (Rudinger, J. & Krejci, I. Experientia 18, (1962), 585–588). $pA_2$ is a measure of the inhibitory effect of the peptide and was defined by Schild (Schild, H. O., British Journal of Pharmacology, 2, (1947), 189–206) as the negative logarithm of the molar concentration of an antagonist which reduces the effect of a dose of agonist to that of half the dose. The agonistic effects, if any, of the antagonists were investigated by adding to the bath containing the uterus preparation a varying amount of peptide corresponding at most to a concentration of 4 μg per ml. No agonistic effect was observed in any of these cases.

IN VIVO TESTS ON RATS

Sprague Dawley rats (250 g) in natural estrous were anaesthetized with Inactin (0.5 mg/100 g body weight i.p.). Myometrial activity was recorded by means of a catheter fixed in the uterine cavity and filled with modified Locke's solution. The catheter was connected to a Statham P23d transducer, and contractions were recorded on a Grass polygraph (model 7d). Oxytocin was infused intravenously (0.05 μg/min/100 g body weight). When a regular contraction pattern had been obtained, the antagonist (0.8–8.0 μg/100 g body weight) was administered intravenously in a volume of 0.2 ml. The recorded curve was integrated over 15 min intervals immediately before and after injection of the antagonist. The inhibition of the increase in the magnitude of the uterus contractions caused by oxytocin infusion Like the Antocin, all of the vasetocin derivatives examined caused a competitive inhibition of the oxytocin effect, as will appear from the $pA_2$ values in Table 3. (It should be mentioned here that $pA_2$ values obtained in different laboratories are not comparable because the test conditions never are equivalent.) The antagonistic values obtained for $pA_2$ show that the derivatives according to the invention have even higher values than the Antocin and thus are even more potent antagonists. The in vivo tests show that the derivatives according to the invention are from 2 to about 18 times more potent antagonists than the Antocin.

In the in vivo tests, the vasotocin derivatives enumerated in Table 3 were capable of completely blocking the contraction pattern of the uterus, i.e. they blocked not only the activity initiated by oxytocin, but also the spontaneous muscle activity of the organ. The doses employed were between 2 and 20 μg per rat.

Table 3 also indicates the antidiuretic effect (AD) and the pressor effect (i.e. the effect on the blood pressure) to show that the resulting values in most cases are so low that these effects need not be taken into consideration upon administration of the vasotocin derivatives according to the invention in order to inhibit uterine contractions. Another important aspect is that all of the vasetocin derivatives showed no agonistic effect when tested on rat uterus preparations in vitro. It may therefore be expected that the derivatives will give no secondary effects.

EXAMPLE OF THE PREPARATION OF A PHARMACEUTICAL COMPOSITION

The vasetocin derivative is taken in an amount of 0.5 mg and dissolved in distilled water together with 5 mg of mannitol. The solution is poured into an ampoule which is sealed and freeze-dried. After storage in freeze-dried condition, the contents of the ampoule may then be diluted with isotonic saline solution to a concentration suitable for administration.

What we claim and desire to secure by Letters Patent is:

1. A vasotocin derivative having the formula

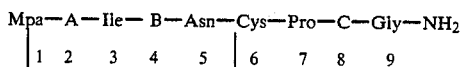

wherein
Mpa is a 3-merceptopropionoyl residue ($-S-CH_2-CH_2-CO-$);
A is the amino acid residue of L- or D-tyrosine-O-ethyl ether (L- or D-Tyr(Et)), or of a hydrophobic D-amino acid,
Ile is the amino acid residue of isoleucine;
B is the amino acid residue of glutamine (Gln), treonine (Thr) or valine (Val);
Asn is the amino acoid residue of asparagin;
Cys is the amino acid residue of cysteine;
Pro is the amino acid residue of proline;
C is the amino acid residue of L- or D-arginine (Arg), ornithine (Orn) or citrullin (Cit); and
Gly—$NH_2$ is the amino acid residue of glycine amide.

2. A vasotocin derivative as claimed in claim 1 in which A is D-Tyr(Et), B is Thr and C is Orn.

3. A vasotocin derivative as claimed in claim 1 in which A is D-Tyr(Et), B is Val and C is Orn.

4. A vasotocin derivative as claimed in claim 1 in which A is D-Trp, B is Val and C is Orn.

5. A pharmaceutical composition for use in the therapeutic treatment of excessive muscle contractions of the uterus comprising at least one derivative according to claim 1 as the active ingredient in combination with pharmaceutically acceptable additives and/or diluents.

6. A pharmaceutical composition as claimed in claim 5 in which a physiological saline solution is present as the pharmaceutically acceptable diluent.

7. An intravenous solution for use in the therapeutic treatment of excessive muscle contractions of the uterus containing as an active ingredient an oxytocin derivative of claim 1 in a physiological saline solution.

8. A solution for use in the therapeutic treatment of excessive muscle contractions of the uterus suitable for intranasal administration comprising an oxytocin derivative as defined in claim 1 dissolved in physiological saline solution.

9. A method of counteracting excessive muscular contractions of the uterus, in which a pharmaceutical composition containing an effective amount of at least one derivative according to claim 1, is administered.

* * * * *